US00PP21538P2

(12) United States Plant Patent
Gilford et al.

(10) Patent No.: US PP21,538 P2
(45) Date of Patent: Nov. 30, 2010

(54) STRAWBERRY PLANT NAMED 'DRISSTRAWTWELVE'

(50) Latin Name: *Fragaria×ananassa*
Varietal Denomination: DrisStrawTwelve

(75) Inventors: Kristie L. Gilford, Lake Placid, FL (US); Esther J. Pullen, Valrico, FL (US); Bruce D. Mowrey, Watsonville, CA (US); Philip J. Stewart, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/587,284

(22) Filed: Oct. 5, 2009

(51) Int. Cl.
*A01H 5/00* (2006.01)

(52) U.S. Cl. ..... Plt./209

(58) Field of Classification Search ..... Plt./209
See application file for complete search history.

*Primary Examiner*—June Hwu
(74) *Attorney, Agent, or Firm*—Jondle & Associates, P.C.

(57) ABSTRACT

This invention relates to a new and distinct variety of strawberry plant named 'DrisStrawTwelve.' The new variety is primarily characterized by having high fruit yield and moderate resistance to *Botrytis* fruit rot, powdery mildew, *Xanthomonas fragariae* and high temperatures.

3 Drawing Sheets

Genus and species: *Fragaria×ananassa.*
Variety denomination: 'DrisStrawTwelve'.

BACKGROUND OF THE NEW PLANT

The present invention relates to a new and distinct strawberry cultivar designated 'DrisStrawTwelve' and botanically known as *Fragaria×ananassa*. This new strawberry cultivar was discovered in Hillsborough, Fla. in December 2004 and originated from a cross between 'Driscoll Sanibel' (U.S. Plant Pat. No. 16,298) and 'Driscoll Bonaire' (U.S. Plant Pat. No. 18,041). The original seedling of the new cultivar was first asexually propagated at a nursery in Shasta County, Calif.

'DrisStrawTwelve' was subsequently asexually propagated in Shasta County, Calif. and underwent further testing Hillsborough, Fla. for four years. The present invention has been found to retain its distinctive characteristics through successive asexual propagations.

DESCRIPTION OF THE PHOTOGRAPHS

The accompanying color photographs show typical specimens of the new cultivar at various stages of development as nearly true as it is possible to make in color reproductions. The photographs were taken from 5-month-old plants.

DESCRIPTION OF THE NEW CULTIVAR

Figure 1:
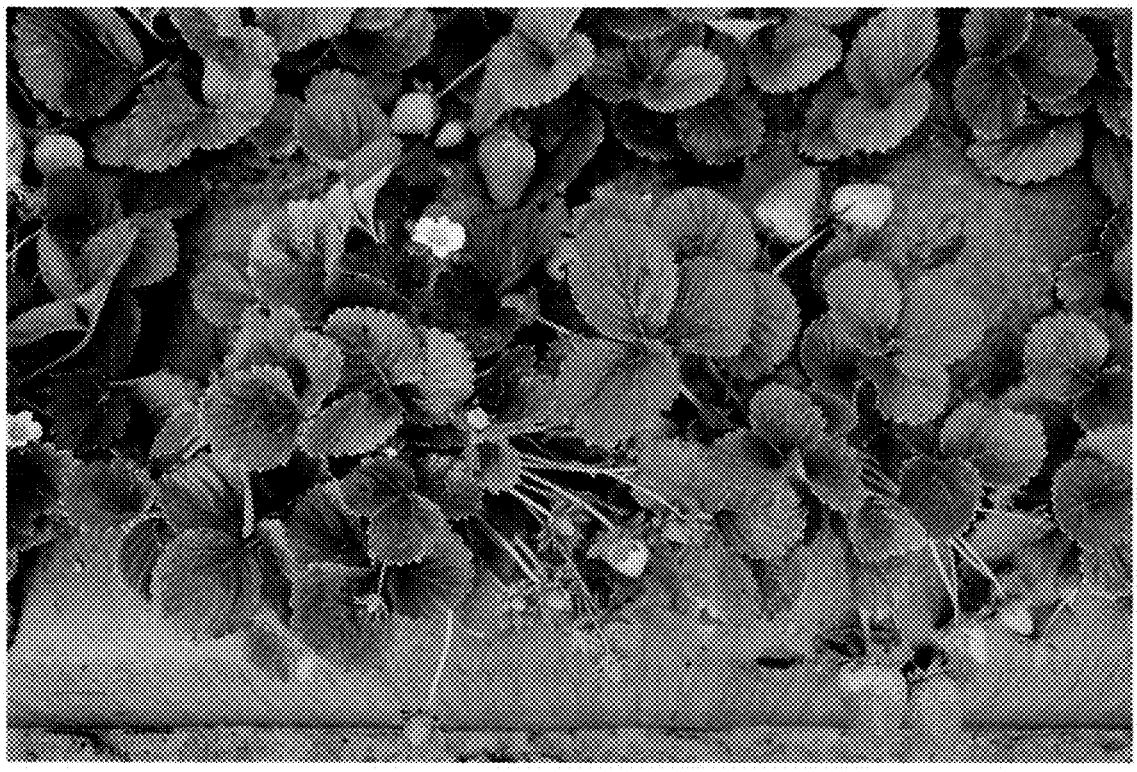
FIG. 1 shows overall plant habit including fruit at various stages of development.
Figure 2:
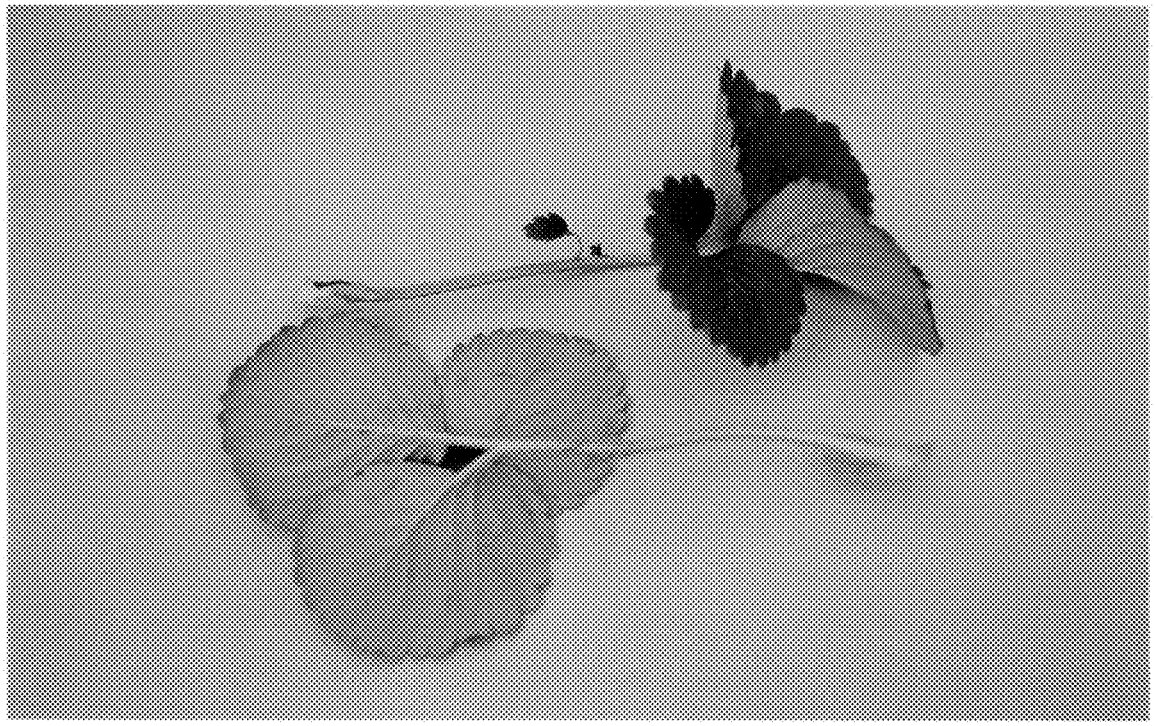
FIG. 2 shows leaves of the plant with three leaflets.
Figure 3:
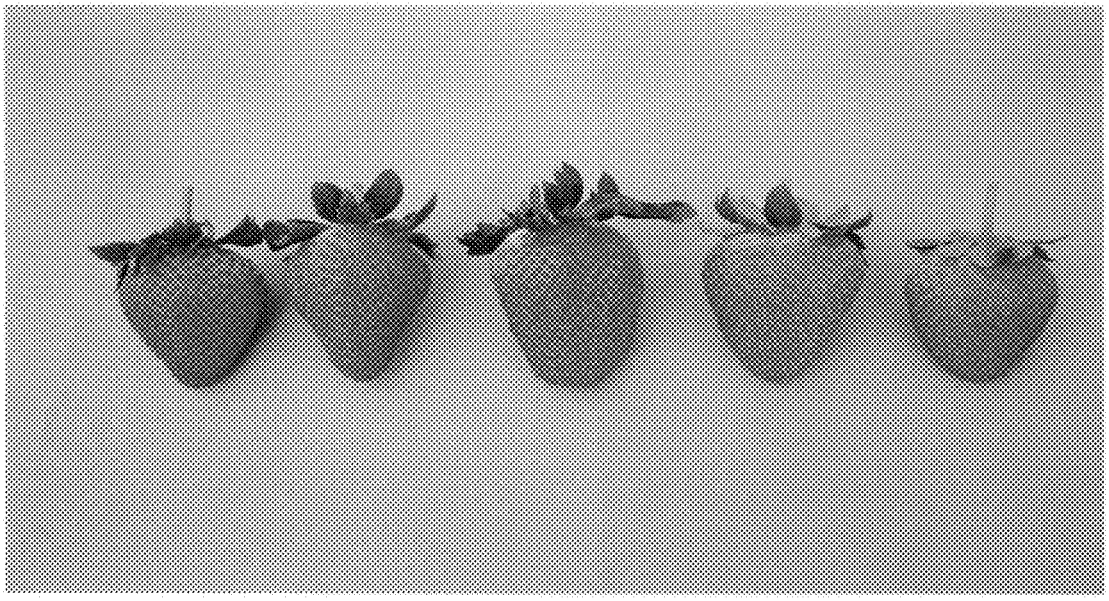
FIG. 3 shows the fruit in longitudinal cross-section.
Figure 4:
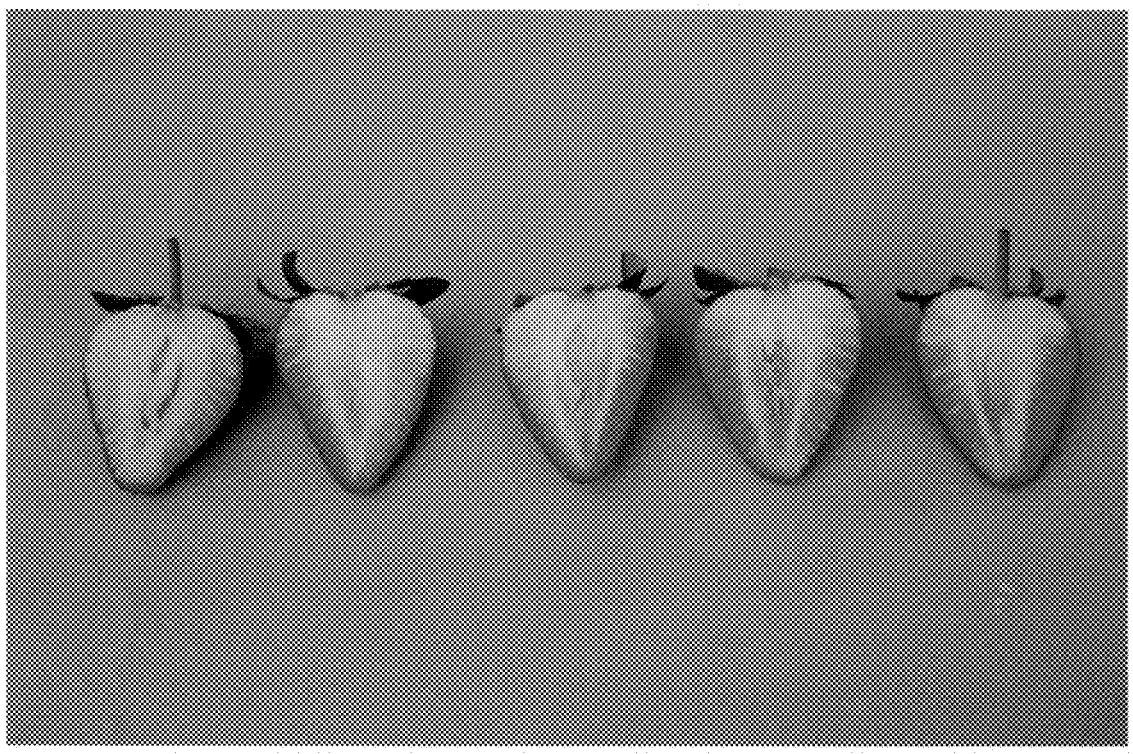
FIG. 4 shows the whole fruit.
Figure 5:
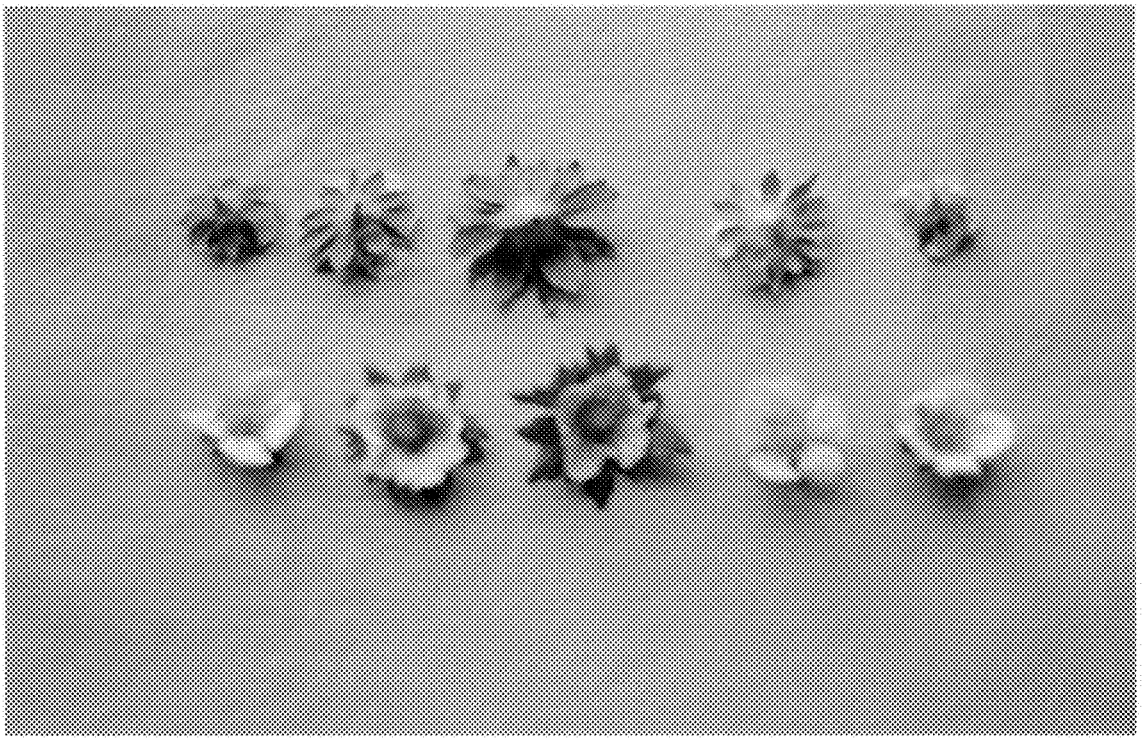
FIG. 5 shows both the upper surface and lower surface of several of the flowers.

The following description of 'DrisStrawTwelve' is based on observations taken in Hillsborough, Fla. from 2005 to 2008. This description is in accordance with UPOV terminology. Color designations, color descriptions, and other phenotypical descriptions may deviate from the stated values and descriptions depending upon variation in environmental, seasonal, climatic and cultural conditions. 'DrisStrawTwelve' has not been observed under all possible environmental conditions. The botanical description of 'DrisStrawTwelve' was taken from 5-month-old plants and the botanical descriptions of the comparison varieties, 'Driscoll Atlantis' (U.S. Plant Pat. No. 16,475) and 'Driscoll Sanibel' (U.S. Plant Pat. No. 16,298), were also taken from 5-month-old plants. Color terminology follows The Royal Horticultural Society Colour Chart, London (R.H.S.) (2001).

DETAILED BOTANICAL DESCRIPTION

Table 1 shows selected plant characteristics of the new variety compared with plant characteristics of 'Driscoll Atlantis' and 'Driscoll Sanibel.' Plant characteristics include plant habit, terminal leaflet length, time of flowering, and fruit production.

TABLE 1

| Characteristic | 'DrisStrawTwelve' | 'Driscoll Atlantis' | 'Driscoll Sanibel' |
|---|---|---|---|
| Plant habit | Flat | Flat globose | Flat |
| Terminal leaflet length | 0.67 cm | 0.73 cm | 0.80 cm |
| Time of flowering | Between early and medium | Between very early and early | Medium |
| Fruit production, grams/plant | 604 | 405 | 420 |

Table 2 shows plant characteristics of the new variety compared with plant characteristics of the commercial varieties 'Driscoll Atlantis' and 'Driscoll Sanibel.' Plant characteristics include plant height, diameter, number of crowns per plant, habit, the density of individual plants and the vigor.

TABLE 2

| Characteristic | 'DrisStrawTwelve' | 'Driscoll Atlantis' | 'Driscoll Sanibel' |
|---|---|---|---|
| Plant height (cm) | 17.5 | 18.8 | 16.0 |
| Plant diameter (cm) | 42.4 | 40.2 | 39.6 |
| Number of crowns/plant | 3 | 3 | 2 |
| Habit | Flat | Flat globose | Flat |
| Density of individual plant | Medium | Medium | Medium |
| Vigor | Between medium and strong | Between weak and medium | Between medium and strong |

Table 3 shows leaf characteristics of the new cultivar compared with leaf characteristics of 'Driscoll Atlantis' and 'Driscoll Sanibel.' Leaf characteristics include terminal leaflet length and width in centimeters, length to width ratio, number of teeth per terminal leaflet, shape of teeth, color of upper side and underside of leaf, leaf shape in cross section, leaf blistering, leaf glossiness, number of leaflets, terminal leaflet margin, terminal leaflet length to width ratio, overall leaf shape and shape of leaf apex and base.

TABLE 3

| Leaf Characteristic | 'DrisStrawTwelve' | 'Driscoll Atlantis' | 'Driscoll Sanibel' |
|---|---|---|---|
| Terminal leaflet length (cm) | 0.67 | 0.73 | 0.80 |
| Terminal leaflet width (cm) | 0.69 | 0.75 | 0.81 |
| Terminal leaflet length/width ratio | 1.0 | 1.0 | 1.0 |
| No. teeth/terminal leaflet | 25 | 23 | 20 |
| Shape of teeth | Rounded | Rounded | Rounded |
| Color of upper surface of leaf | RHS 147A (Dark yellow- green) | RHS 147B (Dark green) | RHS 147A (Dark yellow-green) |
| Color of lower surface of leaf | RHS 148C (Light yellow-green) | RHS 148C (Light yellow-green) | RHS 148C (Light yellow-green) |
| Leaf shape in cross section | Slightly convex | Flat | Slightly convex |
| Leaf blistering | Medium | Medium | Medium |
| Leaf glossiness | Weak | Medium | Medium |
| No. leaflets | 3 only | More than 3 | 3 only |
| Terminal leaflet margin profile | Revolute | Flat | Revolute |
| Terminal leaflet: length/width ratio | As long as broad | As long as broad | As long as broad |
| Terminal leaflet shape | Orbicular | Orbicular | Orbicular |
| Terminal leaflet base shape | Rounded | Rounded | Rounded |
| Terminal leaflet apex shape | Rounded | Rounded | Rounded |

Table 4 shows information about the petiole, the petiolule, the bract, and the stipule of the new cultivar compared to 'Driscoll Atlantis' and 'Driscoll Sanibel.' This includes petiole length in centimeters, petiole diameter in centimeters, petiole pubescence, pose of hairs on the petiole, color of the petiole, color of the petiolule, petiolule length in centimeters, petiolule diameter in centimeters, bract frequency per petiole, stipule length in centimeters, stipule width in centimeters, stipule pubescence and stipule anthocyanin coloration.

TABLE 4

| Characteristic | 'DrisStrawTwelve' | 'Driscoll Atlantis' | 'Driscoll Sanibel' |
|---|---|---|---|
| Petiole length (cm) | 10.0 | 9.9 | 11.1 |
| Petiole diameter (cm) | 0.163 | 0.332 | 0.320 |
| Petiole pubescence | Dense | Medium | Dense |
| Petiole pose of hairs | Upwards and outwards | Outwards | Outwards |
| Petiole color | RHS 145C (Light yellow-green) | RHS 145A (Light yellow-green) | RHS 145C (Light yellow-green) |
| Petiolule color | RHS 145C (Light yellow-green) | RHS 145B (Light yellow-green) | RHS 145C (Light yellow-green) |
| Petiolule length (cm) | 1.208 | 1.023 | 1.033 |
| Petiolule diameter (cm) | 0.060 | 0.178 | 0.182 |
| Bract frequency | 1 | 2 | 1 |
| Stipule length (cm) | 3.0 | 3.3 | 3.0 |
| Stipule width (cm) | 0.783 | 1.048 | 0.968 |
| Stipule pubescence | Medium | Medium | Dense |
| Stipule anthocyanin coloration | RHS 145D (Light yellow-green) | Between weak and medium | |

Table 5 shows stolon characteristics of the new cultivar compared to 'Driscoll Atlantis' and 'Driscoll Sanibel.' These characteristics include the number of stolons, average number of daughter plants, the anthocyanin coloration of the stolons, the thickness of the stolons, and the pubescence of the stolons.

TABLE 5

| Characteristic | 'DrisStrawTwelve' | 'Driscoll Atlantis' | 'Driscoll Sanibel' |
|---|---|---|---|
| Stolon Number | Medium | | |
| Average number of daughter plants | 30 | 53 | 52 |
| Stolon Anthocyanin | RHS 60B (Dark red-purple) | RHS 60A (Dark red-purple) | RHS 53A (Dark red) |
| Stolon Thickness | Medium | Medium | Medium |
| Stolon Pubescence | Sparse | Medium | Medium |

Table 6 shows inflorescence characteristics of the new cultivar compared to 'Driscoll Atlantis' and 'Driscoll Sanibel.' These characteristics include inflorescence position relative to foliage, time of flowering, relative flower size, flower diameter in centimeters (measured from petal tip to petal tip), petal shape, relative spacing of petals, petal apex, base and margin, petal length in centimeters, petal width in centimeters, petal length to width ratio, number of petals, petal color, calyx diameter in centimeters (measured on back of flower from sepal tip to sepal tip), diameter of calyx relative to corolla, diameter of inner calyx relative to outer, sepal shape, apex and margin, sepal length in centimeters (measured from sepal tip to point of attachment to receptacle), sepal width in centimeters, number of sepals, receptacle color and anther color.

TABLE 6

| Characteristic | 'DrisStrawTwelve' | 'Driscoll Atlantis' | 'Driscoll Sanibel' |
|---|---|---|---|
| Inflorescence position relative to foliage | Beneath | Level with | Beneath |
| Time of flowering (50% of plants at first flower) | Between early and medium | Between very early and early | Medium |
| Flower size | Medium | Medium | Large |
| Flower diameter (cm) | 2.457 | 3.019 | 3.147 |
| Petal shape | Orbicular | Orbicular | Orbicular |
| Petal spacing | Overlapping | Overlapping | Overlapping |
| Petal apex shape | Rounded | Rounded | Rounded |
| Petal margin | Entire | Entire | Entire |
| Petal base shape | Rounded | Rounded | Rounded |
| Petal length (cm) | 1.135 | 1.317 | 1.562 |
| Petal width (cm) | 1.136 | 1.460 | 1.492 |
| Petal length/width ratio | As long as broad | Broader than long | As long as broad |
| Typical and observed petal number | 6 | 6 | 7 |
| Petal color | RHS 155B (White) | RHS 155B (White) | RHS 155B (White) |
| Calyx diameter (cm) | 2.902 | 3.064 | 4.834 |
| Calyx diameter relative to corolla | Smaller to same size | Same size | Larger |
| Inner calyx diameter relative to outer | Same size | Same size | Same size |
| Sepal shape | Elliptical | Elliptical | Elliptical |
| Sepal apex shape | Truncate | Truncate | Truncate |
| Sepal margin | Entire | Entire | Entire |
| Sepal length (cm) | 1.001 | 1.131 | 1.661 |
| Sepal width (cm) | 0.514 | 0.546 | 0.785 |
| Typical and observed sepal number | 12 | 12 | 14 |
| Receptacle color | RHS 154B (Light yellow-green) | RHS 2A (Medium yellow) | RHS 150A (Light yellow-green) |
| Anther color | RHS 15A (Medium yellow-orange) | RHS 17B (Dark yellow-orange) | RHS 15A (Medium yellow-orange) |

Table 7 shows fruit characteristics of the new cultivar compared to 'Driscoll Atlantis' and 'Driscoll Sanibel.' These characteristics include fruiting truss length in centimeters, fruiting truss diameter, number of berries per truss, fruiting truss attitude, fruiting truss color, fruit length in centimeters, fruit truss width in centimeters, fruit length to width ratio, fruit hollow length and width in centimeters, fruit hollow length to width ratio, fruit weight in grams, relative fruit size, predominant fruit shape, difference in shape between primary and secondary fruits, band without achenes, unevenness of fruit surface, fruit skin color, evenness of fruit color, fruit glossiness, insertion of achenes, achene coloration (sunward and shaded sides of berry) and the number of achenes per berry.

TABLE 7

| Characteristic | 'DrisStrawTwelve' | 'Driscoll Atlantis' | 'Driscoll Sanibel' |
|---|---|---|---|
| Fruiting truss length (cm) | 16.6 | 21.8 | 14.2 |
| Fruiting truss length-general | Medium | Long | Medium |
| Fruiting truss diameter (cm) at base of truss | 0.267 | 0.282 | 0.285 |

TABLE 7-continued

| Characteristic | 'DrisStrawTwelve' | 'Driscoll Atlantis' | 'Driscoll Sanibel' |
|---|---|---|---|
| Number of berries per fruiting truss | 1 | 2 | 1 |
| Fruiting truss attitude | Prostrate | Semi-erect | Prostrate |
| Fruiting truss color at base of truss | RHS 144B (Medium yellow-green) | RHS 144B (Medium yellow-green) | RHS 144B (Medium yellow-green) |
| Fruit length (cm) | 5.904 | 4.836 | 4.667 |
| Fruit width (cm) | 4.490 | 3.895 | 4.261 |
| Fruit length/width ratio | 1.3 | 1.2 | 1.1 |
| Fruit hollow length (cm) | 2.359 | 1.689 | 0.672 |
| Fruit hollow width (cm) | 0.823 | 0.708 | 0.269 |
| Fruit hollow length/width ratio | 2.9 | 2.4 | 2.5 |
| Fruit weight (g) | 37.9 | 27.3 | 39.0 |
| Relative fruit size | Large | Medium | Medium |
| Predominant fruit shape | Conical to bi-conical | Conical | Conical |
| Difference in shape between primary & secondary fruits | None or very slight | Moderate | Marked |
| Band without achenes | Medium | Medium | Narrow |
| Unevenness of fruit surface | Medium | Medium | Strong |
| Fruit skin color | RHS 185A (Dark purple-red) | RHS 45A (Medium red) | RHS 46A (Dark red) |
| Evenness of fruit color | Slightly uneven | Even | Even |
| Fruit glossiness | Medium | Medium | Between medium and strong |
| Insertion of achenes | Below surface | Below surface | Above surface |
| Achene coloration-sunward side of berry | RHS 184B (Medium greyed-purple) | RHS 181C (Medium greyed-red) | RHS 184B (Medium greyed-purple) |
| Achene coloration-shaded side of berry | RHS 151C (Light yellow-green) | RHS 151B (Light yellow-green) | RHS 151C (Light yellow-green) |
| Achenes per berry | 104 | 114 | 228 |

Table 8 shows fruit characteristics of the new cultivar compared to 'Driscoll Atlantis' and 'Driscoll Sanibel.' These characteristics include the harvest maturity, insertion of calyx, pose of calyx segments, size of calyx in relation to fruit, adherence of calyx, firmness of flesh, color of the fruit flesh, evenness of the flesh color, distribution of flesh color, hollow center, sweetness of fruit, acidity of fruit, texture of fruit when tasted, type of bearing, grams of fruit per plant.

TABLE 8

| Characteristic | 'DrisStrawTwelve' | 'Driscoll Atlantis' | 'Driscoll Sanibel' |
|---|---|---|---|
| Harvest maturity | Mid-December to early April | Early December to March | Mid-December to early April |
| Insertion of calyx | Set above fruit | Level | Level |
| Pose of calyx segments | Spreading to reflexed | Reflexed | Reflexed |
| Size of calyx in relation to fruit | From same size to larger | Same size | From same size to larger |
| Adherence of calyx | Strong | Strong | Strong |
| Firmness of flesh | Firm | Firm | Medium |

TABLE 8-continued

| Characteristic | 'DrisStrawTwelve' | 'Driscoll Atlantis' | 'Driscoll Sanibel' |
|---|---|---|---|
| Color of the flesh | RHS 155B (White) and RHS 42B (Medium Red) | RHS 155D (White) and RHS 40A (Medium red) | RHS 155B (White) and RHS 42A (Medium red) |
| Evenness of flesh color | Even | Even | Even |
| Distribution of flesh color | Marginal and central | Marginal and central | Marginal and central |
| Hollow center | Small | Small | Absent to small |
| Sweetness | Medium | Medium | Between medium and strong |
| Acidity | Weak | Weak | Medium |
| Texture when tasted | Fine | Medium | Medium |
| Type of bearing | Partially everbearing | Partially everbearing | Not everbearing |
| Grams of fruit/plant | 604 | 405 | 420 |

Table 9 shows pest, stress and disease characteristics of the new cultivar compared to 'Driscoll Atlantis' and 'Driscoll Sanibel'.

TABLE 9

| Pest, Stress or Disease | 'DrisStrawTwelve' | 'Driscoll Atlantis' | 'Driscoll Sanibel' |
|---|---|---|---|
| *Botrytis* fruit rot | Moderately resistant | Susceptible | Susceptible |
| Powdery mildew | Moderately resistant | Susceptible | Susceptible |
| *Xanthomonas fragariae* | Moderately resistant | Between resistant and moderately resistant | Between resistant and moderately resistant |

TABLE 9-continued

| Pest, Stress or Disease | 'DrisStrawTwelve' | 'Driscoll Atlantis' | 'Driscoll Sanibel' |
|---|---|---|---|
| High temperatures | Moderately resistant | Moderately resistant | Resistant |

COMPARISON WITH PARENTAL AND COMMERCIAL CULTIVARS

When 'DrisStrawTwelve' is compared to the female parent 'Driscoll Sanibel' (U.S. Plant Pat. No. 16,298), 'DrisStrawTwelve' has greater fruit production, larger fruit and fewer daughter plants than does 'Driscoll Sanibel.' In addition, 'DrisStrawTwelve' has moderate resistance to *Botrytis* fruit rot and powdery mildew while 'Driscoll Sanibel' is susceptible to both diseases.

When 'DrisStrawTwelve' is compared to the male parent 'Driscoll Bonaire' (U.S. Plant Pat. No. 18,041), 'DrisStrawTwelve' is a taller plant with dark yellow-green leaves than 'Driscoll Bonaire' which has medium green leaves. In addition, 'DrisStrawTwelve' produces more fruit than 'Driscoll Bonaire' although 'DrisStrawTwelve' has fewer daughter plants. 'DrisStrawTwelve' is also moderately resistant to *Botrytis* fruit rot while 'Driscoll Bonaire' is susceptible; 'DrisStrawTwelve' is moderately resistant to powdery mildew and *Xanthomonas fargariae* while 'Driscoll Bonaire' is moderately susceptible to both diseases.

We claim:

1. A new and distinct variety of strawberry plant as described and shown herein.

* * * * *